(12) United States Patent
Moneymaker et al.

(10) Patent No.: US 7,785,619 B2
(45) Date of Patent: *Aug. 31, 2010

(54) PHARMANUTRIENT COMPOSITION(S) AND SYSTEM(S) FOR INDIVIDUALIZED, RESPONSIVE DOSING REGIMENS

(75) Inventors: Ricky Dean Moneymaker, Stuart's Draft, VA (US); Larry Scott Klesman, Lake Forest, IL (US); Jon Scott Theus, Gurnee, IL (US)

(73) Assignee: Micro Nutrient, LLC, Lincolnshire, IL (US)

( * ) Notice: Subject to any disclaimer, the term of this patent is extended or adjusted under 35 U.S.C. 154(b) by 634 days.

This patent is subject to a terminal disclaimer.

(21) Appl. No.: 11/080,790

(22) Filed: Mar. 15, 2005

(65) Prior Publication Data

US 2005/0226907 A1    Oct. 13, 2005

Related U.S. Application Data

(63) Continuation-in-part of application No. 10/868,149, filed on Jun. 15, 2004, now abandoned.

(60) Provisional application No. 60/561,097, filed on Apr. 8, 2004.

(51) Int. Cl.
   *A61F 13/00* (2006.01)
(52) U.S. Cl. .................................. 424/435; 424/439
(58) Field of Classification Search ................ None
   See application file for complete search history.

(56) References Cited

U.S. PATENT DOCUMENTS

| | | | |
|---|---|---|---|
| 4,882,167 A | | 11/1989 | Jang |
| 5,629,003 A | | 5/1997 | Horstmann et al. |
| 5,643,623 A | | 7/1997 | Schmitz et al. |
| 5,770,215 A | * | 6/1998 | Moshyedi ................ 424/440 |
| 5,932,624 A | | 8/1999 | Herbert |
| 5,948,430 A | | 9/1999 | Zerbe et al. |
| 6,030,650 A | | 2/2000 | Kamarei |
| 6,048,846 A | * | 4/2000 | Cochran ................ 514/168 |
| 6,054,477 A | | 4/2000 | Harris |
| 6,080,431 A | | 6/2000 | Andon et al. |
| 6,207,203 B1 | | 3/2001 | Atkinson et al. |
| 6,228,388 B1 | | 5/2001 | Paradissis |
| 6,248,363 B1 | | 6/2001 | Patel et al. |
| 6,264,981 B1 | | 7/2001 | Zhang et al. |
| 6,265,438 B1 | | 7/2001 | Steward |
| 6,299,886 B1 | | 10/2001 | Piper |
| 6,299,896 B1 | | 10/2001 | Cooper et al. |
| 6,316,029 B1 | | 11/2001 | Jain et al. |
| 6,361,800 B1 | | 3/2002 | Cooper et al. |
| 6,375,963 B1 | | 4/2002 | Repka et al. |
| 6,387,381 B2 | | 5/2002 | Christensen |
| 6,419,903 B1 | | 7/2002 | Xu et al. |
| 6,488,956 B1 | | 12/2002 | Paradissis |
| 6,497,899 B2 | | 12/2002 | Thombre et al. |
| 6,528,088 B1 | | 3/2003 | Gilleland et al. |
| 6,569,463 B2 | | 5/2003 | Patel et al. |
| 6,592,887 B2 | | 7/2003 | Zerbe et al. |
| 6,596,298 B2 | | 7/2003 | Leung et al. |
| 6,605,646 B2 | | 8/2003 | Herbert |
| 6,703,371 B1 | * | 3/2004 | Wiss ........................ 514/23 |
| 7,078,016 B2 | * | 7/2006 | Rabinowitz ............... 424/45 |
| 2001/0036464 A1 | | 11/2001 | Christensen |
| 2003/0099753 A1 | * | 5/2003 | Yang ...................... 426/599 |
| 2003/0148992 A1 | * | 8/2003 | Block et al. ............... 514/52 |
| 2003/0194431 A1 | | 10/2003 | Miller et al. |
| 2004/0001817 A1 | * | 1/2004 | Giampapa ............... 424/94.1 |
| 2004/0001874 A1 | | 1/2004 | Davidson et al. |
| 2004/0043134 A1 | * | 3/2004 | Corriveau et al. ......... 426/658 |
| 2004/0120991 A1 | * | 6/2004 | Gardner et al. ........... 424/443 |
| 2004/0191377 A1 | | 9/2004 | Malleshi et al. |

FOREIGN PATENT DOCUMENTS

| | | |
|---|---|---|
| EP | 0390435 A | 10/1990 |
| GB | 1420883 A | 1/1976 |
| WO | WO 99/17753 | 4/1999 |
| WO | WO-04/000297 A | 12/2003 |
| WO | WO04/000297 A1 | 12/2003 |

(Continued)

OTHER PUBLICATIONS

Wikipedia p. 1-7, search pyridoxine and pantothenic "http://en.wikipedia.org/wiki/Pyridoxine" and "http://en.wikipedia.org/wiki/Pantothenic_acid".*

(Continued)

*Primary Examiner*—Robert A Wax
*Assistant Examiner*—Bethany Barham
(74) *Attorney, Agent, or Firm*—McAndrews Held & Malloy, Ltd.

(57) ABSTRACT

Individualized responsive dosing pharmanutrient systems, compositions, methods of dosing, and processes of producing the same, which allow a consumer to generate individualistic biological responses/effects. More specifically, a pharmanutrient system for generating individualized biological conditions/responses which utilizes ultra-low dosage amounts of vitamins, minerals, amino acids, co-enzymes, organics substrates, inorganic or synthetic substrates, biological components, and/or other nutrients incorporated or provided with a pharmacologically active ingredient in a bio-active delivery system which preferably avoids first pass metabolism, such that an individual may take multiple doses of the same or different pharmanutrient based on varying desired biological response within each dosing period.

2 Claims, No Drawings

FOREIGN PATENT DOCUMENTS

| WO | WO-2004/086881 A | 10/2004 |
|---|---|---|
| WO | WO2004086881 | 10/2004 |

OTHER PUBLICATIONS

Shrimpton, Derek; "RDAs—what do they really mean", The Pharmaceutical Journal, vol. 268, Mar. 16, 2002.*
http://en.wikipedia.org/wiki/Soybean (p. 1).*
http://en.wikipedia.org/wiki/Whey_protein (p. 1).*
D. J. Birkett, *Bioavailability and First Pass Clearance*, Australian Prescriber, vol. 14, No. 1 (1991).
Jesse F. Gregory, *Case Study: Folate Bioavailability*, American Society for Nutritional Sciences, 0022-3166/01 (2001), pp. 1376S-1382S.
Allison A. Yates, *National Nutrition and Public Health Policies: Issues Related to Bioavailability of Nutrients When Developing Dietary Reference Intakes*, American Society for Nutritional Sciences, 0022-3166/01 (2001), pp. 1331S-1334S.
Workshop Proceedings, Workshop on the Role of Dietary Supplements for Physically Active People, National Institutes of Health (Jun. 3-4, 1996).
B. Jasti, et al., *Recent Advances in Mucoadhesive Drug Delivery Systems*, Business Briefings: Pharmatech (2003), pp. 194-196.
A. Shojaei, *Buccal Mucosa as a Route for Systemic Drug Delivery: A Review*, J. Pharm. Pharmaceut. Sci. 1(1): 15-30 (1998).
Office Action Summary mailed Mar. 16, 2009 for U.S. Appl. No. 11/483,208, filed Jul. 7, 2006.
Office Action Summary mailed Sep. 24, 2007 for U.S. Appl. No. 11/483,208, filed Jul. 7, 2006.
Office Action Summary mailed Jan. 2, 2008 for U.S. Appl. No. 11/483,208, filed Jul. 7, 2006.
Office Action Summary mailed May 13, 2008 for U.S. Appl. No. 11/483,208, filed Jul. 7, 2006.
Office Action Summary mailed Aug. 5, 2008 for U.S. Appl. No. 11/483,208, filed Jul. 7, 2006.
Office Action Summary mailed Mar. 16, 2009 for U.S. Appl. No. 11/483,208, filed Jul. 7, 2006.
"Dietary Reference Intakes for Water, Potassium, Sodium, Chloride, and Sulfate", www.nap.edu. Copyright 2004 by The National Academies.
Notification of the First Office Action for Chinese Patent Application No. 200580016730X issued Dec. 5, 2008.
Notification Concerning Transmittal of International Preliminary Report on Patentability mailed Oct. 19, 2006 for International Application No. PCT/US2005/008599.
Written Opinion of the International Searching Authority for International Application No. PCT/US2005/008599 received Aug. 11, 2005.
Notification of Transmittal of the International Search Report & the Written Opinion of the International Searching Authority dated Aug. 16, 2005 for International Application No. PCT/US2005/008599.
PCT International Search Report for PCT/US2005/008599 dated Aug. 16, 2005.
Communication from the European Patent Office dated Dec. 20, 2007 for Application No. 05 730 880.0-2108.
International Search Report for PCT/US04/19243 dated Jun. 7, 2005.
Written Opinion of the International Searching Authority for PCT/US04/19243 dated Jun. 7, 2005.

* cited by examiner

PHARMANUTRIENT COMPOSITION(S) AND SYSTEM(S) FOR INDIVIDUALIZED, RESPONSIVE DOSING REGIMENS

RELATED APPLICATIONS

This application is a continuation-in-part application claiming priority to non-provisional U.S. application Ser. No. 10/868,149, filed on Jun. 15, 2004, now abandoned, which further claims priority to pending provisional U.S. Application Ser. No. 60/561,097, filed on Apr. 8, 2004 each of which are incorporated by reference herein in their entirety.

FIELD OF THE INVENTION

The present technology relates generally to individualized, responsive dosing pharmanutrient products and/or systems, compositions, methods of treatment, and processes of producing the same, which allow a consumer to target identifiable, individualistic biological conditions or attendant responses thereto. More specifically, the present technology relates to a pharmanutrient product and/or system for targeting individualized biological conditions or attendant responses which utilizes ultra-low dosage amounts of vitamins, minerals, amino acids, co-enzymes, stimulants, and/or similar ingredients in a highly bio-active delivery system, which are further delivered with and/or incorporated with a pharmacologically active ingredient such that an individual may take multiple doses of the same or different pharmanutrient mixture based on varying biological need or desired response within each 24 hour period.

BACKGROUND

Vitamins, minerals, amino acids, co-enzymes and the like are compounds required by an animal or human body in varying amounts for the purposes of metabolism, biophysiological repair, immunity, growth, and cellular function and/or reproduction. These compounds also assist in the formation or control of hormones, blood cells, nervous-system chemicals, and genetic material.

Vitamins, minerals, amino acids, and co-enzymes are often referred to as nutrients, defined herein as a substance or ingredient which may be found in food which imparts a medicinal or health benefit. The various nutrient compounds are not chemically related, and most differ in their physiological actions. They generally act as catalysts, combining with proteins (or other biological substrates) to create metabolically active enzymes (or other biological components) that in turn produce hundreds of important chemical reactions and responses throughout an animal or human body. Without nutrients, many of these reactions would slow down or cease. The intricate ways in which nutrients act on the body, however, are still far from clear. The Food and Nutrition Board of the National Research Council replaced and expanded the Recommended Dietary Allowances (RDAs) with Dietary Reference Intakes (DRIs) to provide recommended vitamin, mineral, or other nutrient intakes for use in a variety of settings for humans.

The DRIs are actually a set of four reference values: Estimated Average Requirements (EAR), Recommended Dietary Allowances (RDA), Adequate Intakes (AI), and Tolerable Upper Intake Levels (UL). These values serve as recommended dosage levels for vitamins, minerals, or other nutrients. Currently there are no DRI's for intake of caffeine and other stimulants, or for L-glutamine or L-arginine. However, the U.S. National Library of Medicine and the National Institute of Health recommend, for example, that for caffeine, no more than 200 milligrams should be taken every three or four hours by an adult human, and that an adult human should not take more than 1600 mg in a twenty-four hour period. Additionally, L-arginine is typically provided in dietary supplements in dosages of about 100 milligrams, and L-glutamine in dosages of about 500 milligrams, pursuant to the guidelines of the United States Food & Drug Administration.

Pharmanutrients are generally referred to and described herein as a vitamin, mineral, amino acid, herb, botanical, or dietary substance which may be further delivered in some manner with or incorporated with a pharmacologically active ingredient for use to supplement an animal or human diet, treat an animal or human biological condition or disease state condition, or used to generate a biological response. Additionally, a pharmacologically active ingredient is generally referred to and described herein as any drug component that is intended to furnish pharmacological activity or other direct effect in the diagnosis, cure, mitigation, treatment, or prevention of disease, or to affect the structure or function of the body of a human or animal. Thus, a pharmacologically active ingredient envisions not only prescription medications, but those that are considered non-prescription and/or over-the-counter (OTC) medications as well.

Dietary supplements are generally nutrient mixtures commonly taken in single standard and/or mega-dose dosage forms which contain vitamin, mineral and other nutrient doses equal to or over the Recommended Dietary Allowances (RDA) values. Although standard and/or mega-dose regimens are a common practice for the prevention of disease, there is a great deal of debate in the literature and medical community regarding the efficacy of such regimens. Moreover, consuming conventional large doses (i.e., standard or mega-dose) of vitamins, minerals, or other nutrients, in the absence of some deficiency and/or disease state, or without proper medical supervision, may cause harmful toxic effects and/or result in hypervitaminosis. The same can also be said of currently available pharmacologically active ingredients with or without conventional dosing and/or medical supervision with respect to the dosing regimens of those materials and their attendant side effect profiles.

Additionally, a consumer usually has little choice in choosing the variety of ingredients, dosage levels, or dosing regimens of a conventional dietary supplement or pharmanutrient product. Conventional dietary supplements, for example, tableted vitamins, may be effective for a general nutrient supplementation purpose, but usually provide an excess of vitamins, minerals, stimulants, or other ingredients which a consumer does not desire or require. Further, those same supplements may not adequately target an individual's specific dietary need or desired biological response at any given time. Moreover, conventional dosage forms of dietary supplements, nutrients, and pharmanutrients typically only allow a consumer to take one or two doses per any given twenty-four (24) hour period. As a result, conventional dietary supplements and pharmanutrients fail to recognize that the physiological state and resultant nutrient or pharmacologically active ingredient requirements of any single individual can depend upon and fluctuate based upon a number of different biophysical variables during the course of each day or dosing regimen period. For example, individual variations in diet as well as the amount and intensity of physical activity, provide physical and chemical stimuli that stress various systems of the body to differing degrees from one person to the next on any given day. Thus, conventional "one size fits all" nutrient, pharmanutrient, and individual pharmacological active ingredient mega-dose dosage forms/regimens are not amenable to empirical, individualized dosage adjustment to achieve an individualized biophysiological objective or response for various biological conditions or events.

Another drawback with most conventional dietary supplements, nutrients, or pharmanutrient product/systems is that they suffer from poor degrees and/or rates at which the various nutrients or active ingredients contained therein are absorbed into the systemic circulation of the human or animal body and made available for biophysiological activity (e.g., "bioavailability"). These degrees or rates of bioavailability typically depend upon the dose, dosage form, and method of administration of the various nutrients or active ingredients to the human or animal body.

One particular barrier to efficient nutrient or pharmacologically active ingredient bioavailability is "first-pass metabolism", which is defined herein to mean a process in which the nutrient compound(s) or pharmacologically active ingredient(s) are modified, activated, or inactivated before they enter the systemic circulation, or is left unchanged and excreted. Alternatively, first-pass metabolism may be defined as the intestinal and hepatic degradation or alteration of a drug (i.e., pharmacologically active ingredient), nutrient, or other substance orally, and after absorption, removing some of the absorbed substance (i.e., active ingredient or nutrient) from the blood before it enters the general circulation to generate a biological response or effect.

For example, it is believed by some within the medical and dietary supplement communities that one significant drawback to "mega-dosing" of vitamins, minerals, other nutrients or pharmacologically active ingredients/drugs is that increased dosages may not be adequately absorbed into the human or animal body, or may actually decrease absorption. Thus, available transport mechanisms may become saturated and unable to absorb excess dose. Additionally, another drawback to vitamin, mineral, or drug delivery via a conventional tablet or capsule is that differences in luminal pH along the gastrointestinal tract lining, surface area per luminal volume, blood perfusion, presence of bile and mucus, and the nature of epithelial membranes may prevent efficient absorption, activation, and the like of a nutrient or drug, thereby decreasing the bioavailability of each. Additionally, as side effects are increased and/or the desired biological response, effect, or affect is decreased, individuals taking such conventional "mega-dose" supplements or pharmanutrients tend to become mal- or non-compliant. Thus, the current norm for temporal dynamics associated with such conventional therapies is lessened or prevented.

To compensate for first pass metabolism effects, some previous efforts have been directed to enterically coated tablets or capsular dosage forms which pass through the stomach unaltered to disintegrate in the lower intestines to attempt to achieve increased absorption of the nutrient or drug. However, aside from a delayed biophysiologic response as gastric emptying becomes rate-limiting, gastric irritability, and potential allergic reactions from the ingestion of such coating materials generally occur. Further, enterically coated delayed release dosage forms must dissolve and typically be absorbed within a narrow time frame. As a result, the human or animal body typically excretes the non-absorbed nutrient or drug rather than fully absorb and utilize either.

Additional previous attempts at minimizing first pass metabolism effects to increase the bioavailability of a nutrient or pharmacologically active ingredient have also been directed to continuous or gradual release dosage forms. U.S. Pat. No. 4,882,167, to Jang, discloses dry direct compressed products for controlled release of actives including vitamins or minerals. However, the compositions and methods of the Jang patent do not provide for ultra-low dosage amounts of vitamins or minerals, dosing flexibility, or a type of system, composition, or method for individualized, responsive dosing based on a desired and/or targeted biological response/effect/affect.

WO 99/17753 discloses rapidly dissolving films for delivery of drugs to be adsorbed in the digestive tract. U.S. Pat. No. 6,596,298, to Leung, discloses consumable oral care films which may optionally contain active amounts of pharmacologically active ingredients/drugs. However, these patents do not utilize vitamins or minerals, and more specifically, ultra-low dosage amounts of nutrients which would operate to provide flexibility for individualized dosing alone, or in conjunction or concert with, or in combination with a drug. Moreover, these products or processes do not provide a system or selection for varying the type or level of dosage depending on a biological response/effect/affect desired.

Therefore, there is presently a need for an efficient process for producing a pharmanutrient composition, dosing regimen and delivery system that is capable of individualized biologically responsive dosing (i.e., dosing based upon empirical analysis and adjustment), which is available in a suitable dosage form, and preferably is efficiently absorbed and made bioavailable to animal or human tissue. Additionally, there is presently a need for a treatment method for managing finely tuned biological needs and responses which utilizes ultra-low dosage amounts of nutrients, varied dosage amounts of a drug, substantially avoids first-pass metabolism, and allows for varied dosage/dosing regimens within each dosing period (e.g., 24 hours, 6 hours, 1 hour, 30 minutes, etc.).

SUMMARY OF THE INVENTION

Embodiments of the presently described technology provide one or more of the following advantageous features and/or objects:

(1) Production of varied and separate pharmanutrient composition series that are configured to generate discrete types of biological responses/effects/affects in the body;

(2) Production of a range or series of ranges of pharmanutrient compositions containing varying levels or ranges of nutrient and/or pharmacologically active ingredients administered separately, but in conjunction or concert with each other in a variety of final compositions and dosage forms individually, or incorporated together into a variety of final compositions and dosage forms to generate varying levels or ranges of biological responses/effects/affects in an animal or human body;

(3) Efficient rate of absorption into an animal or human body to improve bioavailability, biokinetics, and biodelivery;

(4) Efficient bioavailability of multiple vitamins, minerals, amino acids, co-enzymes, other nutrient compounds, and/or drugs and the like in concert;

(5) Avoidance of first pass metabolism effects, transport mechanism saturation, or excretion of significant amounts of a pharmanutrient composition;

(6) A biological response equivalent pharmanutrient dosing unit that does not approach RDA or UL amounts, but is still effective in enhancing the overall well being of an individual and generating a biological response;

(7) The ability to take multiple doses of a single finely tuned pharmanutrient composition as need varies within each desired time period (i.e., week, day, hour, minute and the like); and (8) The ability to take multiple doses of different finely tuned pharmanutrient compositions as different needs develop during each week, day, and/or hour.

Other objects and advantages of the presently disclosed technology will become apparent to those skilled in the art who have the benefit of this specification and the prior art.

In preferred embodiments of the presently described technology, there are provided processes for producing an individualized responsive dosing pharmanutrient system(s) and processes, the resultant products of such processes, compositions for use in an individualized responsive dosing pharmanutrient system(s), and a method for generating a biological response utilizing such a system(s).

The process for producing an individualized responsive dosing pharmanutrient system(s) preferably first comprises a starting water source which preferably contains beneficial, but ultra low dosage levels of at least one mineral and optionally, at least one nitrate and at least one nitrite. A base mixture is then added containing at least two vitamins and/or minerals, which are selected from a group of two or more base compositions configured to generate one or more pre-determined biological responses/effects/affects, and at least one pharmacologically active ingredient (i.e., drug). The base mixture is preferably selected based on a desired biological response/effect/affect basis for the finished pharmanutrient composition. A pre-mix composition, which is preferably of a constant compositional make-up during different formulating stages of the process, is then added or, alternatively, is added as part of the base mixture. Alternatively, the pre-mix composition may be added in different formulating stages of the process as described herein at different concentrations as a function of the specific affects/effects/responses as desired.

It will also be understood that the base mixture can also optionally be varied in intensity or effectiveness by aging the base mixture for a period of time ranging from about 48 hours to about 240 hours. By aging the base mixture, it has been observed that the effects in the ranges as described in Example 15 below could be achieved and/or maintained. It is believed that the life span or shelf-life of the base mixture alone is approximately twenty-eight days if base mixture aging is utilized in the spirit and scope of the presently described technology.

Optionally, the mixture comprising the water, base mixture, and pre-mix, may then be further diluted based on a pre-determined dilution factor, to vary the ultimate dosage levels in the finished pharmanutrient composition. Alternatively, the amount of base mixture may be varied during processing based on a pre-determined multiplier.

Then, the mixture containing water, base mixture, and pre-mix, and optionally further water, is configured into or onto a delivery system (such as, but not limited to an oral film) which substantially avoids first-pass metabolism, to form a finished single nutrient composition. Additionally, it is preferable that the dosage level of any vitamin, mineral, amino acid, co-enzyme, or other nutrient contained in the finished pharmanutrient compositions of the presently described technology be less than 25% of the RDA or UL for such vitamin, mineral, amino acid, co-enzyme, or other nutrient. More preferably, the dosage levels are less than 10%, 1%, or 0.1% of RDA or UL for each nutrient. In the most preferred instances, the dosage levels are less than 0.001% or less than 0.0001% of RDA or UL. Preferably, however, the dosage levels are at least $1 \times 10^{-7\%}$ of RDA or UL. An illustrative formulation for a finished single dose (5 drops) of a final nutrient formulation without incorporation of a pharmacologically active ingredient in a liquid delivery system of the present technology is given in Example 17, below.

Finally, the foregoing process steps may be repeated one or more times, more preferably five or more times, and most preferably, ten or more times, and either a different base mixture is selected, or a different dilution or base multiplication factor is selected, or base aging is utilized to produce a system/series of pharmanutrient compositions capable of being utilized for individualized biological responsive dosing.

Other embodiments of the presently described technology set forth below illustrate the resultant products of such a process(es) for the production of an individualized responsive dosing pharmanutrient system, as well as specific base mixtures and pre-mix compositions for use in such-process and system(s).

Additionally, there is presently described a method for individualized responsive dosing to generate a biological response/effect/affect or to treat a biological condition, comprising the steps of providing a selection of one or more pharmanutrient formulations in delivery systems which substantially avoid first pass metabolism and which provide two or more vitamins, minerals, amino acids, co-enzyme, or other nutrients in amounts preferably less than 10% or 1% of RDA or UL, more preferably less than 0.01% of RDA or UL, and most preferably less than 0.0001% of RDA or UL, a water source comprising at least one mineral and/or other nutrients, a sufficient amount of a pharmacologically active ingredient (i.e., drug) and optionally at least one nitrate and/or at least one nitrite in amounts preferably less than 0.001% of RDA or UL. Preferably, however, the dosage levels for nutrients within the pharmanutrient composition of the presently described technology are at least $1 \times 10^{-7\%}$ of RDA or UL.

The one or more pharmanutrient compositions and/or systems are preferably separately configured to generate one or more pre-determined biological responses/effects/affects, including, but not limited to general metabolic system control and modulation, stress-relief, cellular metabolism, preventative or remedial anti-aging, hormonal release, improved cardiovascular outcomes (e.g., decreased hypertension and decreased atherosclerotic plaque deposition), energy conservation, modulated neurochemical release or uptake, energy utilization, glucose modulation, energy enhancement, cellular repair, enhanced memory, enhanced cognitive function, calmness, awareness, elimination or excretion of cellular or tissue by-products (e.g., ammonia), stimulation of the hypothalamic-pituitary-thyroid axis, fatigue relief, enhanced immune response modulation, antioxidation, liver detoxification, alcohol metabolism, modulation of tissue catabolic activity, syndrome metabolism modulation, fertility modulation, improved lymphatic system control, satiety modulation, weight modulation, oxygen metabolism modulation, pyruvate/lactic acid metabolism modulation, mitochondrial function modulation, and digestive enhancement.

Additional embodiments are disclosed in the detailed description provided below. While the presently described technology will be provided in connection with one or more preferred embodiments, it will be understood by those skilled in the art that the presently described technology is not limited to those embodiments. To the contrary, the presently described technology includes all alternatives, modifications, and equivalents as may be included within the spirit and scope of the appended claims.

DETAILED DESCRIPTION OF THE INVENTION

It has been unexpectedly and surprisingly discovered that the dose of a vitamin(s), mineral(s), or other nutritional supplement ingredient(s), and/or a pharmacologically active ingredient(s), when adapted for delivery via a unitary dosage form (or alternatively separate dosage forms provided in conjunction or concert with one another in the described manners below) that substantially avoids first pass metabolism, may be significantly reduced (relative to conventionally utilized dosages) while still producing a desired beneficial effect/biological response/biological affect. As a result, the nutrient ingredients and potentially, the pharmacologically active ingredients of a pharmanutrient formulation may be provided at substantially lower levels (i.e., ultra-low levels) than those recommended by the government (i.e., United States Food & Drug Administration) as a raw material standard (RDA, UL, UDA, etc.) for nutrients or standard doses regarding accepted and approved drug components.

Furthermore, it has been surprisingly discovered that such ultra-low dosage levels and bioactive delivery systems allow pharmanutrient compounds to be repeatedly and flexibly administered to an animal or human for the enhancement and augmentation of those biological functions known to be influenced by any of the individual components. These biological functions include without limitation those processes associated with: cellular metabolism including nucleic acid and amino acid metabolism; energy metabolism including energy conversion, utilization, and enhancement; syndrome metabolism, oxygen metabolism; mental acuity including memory and cognitive function; elimination of cellular or tissue by-products (e.g., ammonia); immune response regulation; the nervous system including neuromuscular production, transmission propagation, and/or repair (e.g., neurodegenerative states); hormonal responses including stimulation of the hypothalamic-pituitary-thyroid axis or regulation of glucose production and consumption; management of peripheral and central fatigue including the enhancement of antioxidant defense systems; the mitigation of episodic and/or chronic stress; and detoxification by the liver including increased alcohol metabolism.

Specifically, it is believed that due to the unique combination of ultra-low nutrient dosage levels in combination and/or in concert with the pharmacologically active ingredients utilized in the present technology, a specific composition may be taken by an individual or prescribed by a health care provider multiple times within each dosing period (e.g., within each 24 hour, 6 hour, or 1 hour, or 30 minute period of time and the like). Alternatively, an individual may take or a health care provider may prescribe multiple, different pharmanutrient compositions of the present technology within a dosing period to generate varied biological responses, affects, or effects. Thus, the presently described technology may be utilized in a system which allows an individual or health care provider to, in essence, biologically configure one's pharmanutrient intake throughout a dosing period or multiple dosing periods, based on their individual needs and assessed biological responses.

Accordingly, the presently described technology describes processes for producing an individualized biologically responsive dosing pharmanutrient system and process, the resulting products of such processes, compositions for use in an individualized responsive dosing system, and a method of treatment for generating a biological response(s)/effect(s)/affect(s) utilizing the individualized responsive dosing system.

In one embodiment of the present technology, there is provided a process for producing an individualized biologically responsive dosing system that as a pharmanutrient, first comprises a starting water source which preferably contains beneficial, but ultra-low dosages of at least one mineral and/or other nutrients and optionally, at least one nitrate and at least one nitrite. A base mixture which comprises at least two vitamins, minerals, or other nutrients, more preferably at least three vitamins or minerals, and most preferably at least five such nutrients as well as a pharmacologically active ingredient is added to the water. The base mixture is preferably selected from a group of two or more base mixtures configured to generate one or more pre-determined biological effects. More preferably, the base mixture is selected from a group of five or more base mixtures, and most preferably, a group of 10 or more. The base mixture is preferably selected based on a desired biological response/effect/affect for the finished pharmanutrient formulation.

Next, a pre-mix composition, which preferably comprises constant percentage ratios of certain vitamins, minerals, amino acids, co-enzymes, or other nutrients during processing, is either added separately or, more preferably, is included as part of the base mixture during preparation to a final, finished pharmanutrient formulation. The pre-mix, discussed in detail below, preferably contains at least three or more, and more preferably, at least five or more, different vitamins, minerals, amino acids, co-enzymes, and/or other nutrients.

Optionally, as an alternative embodiment, an intermediate mixture comprising the water, base mixture, and pre-mix may be further diluted based on a preferably pre-determined dilution factor, to vary the ultimate dosages of the nutrients in the final formulation. This enables a manufacturer to easily create a range of dosage formulations. Alternatively, the amount of base mixture may be varied during processing based on a multiplier. Both the multiplier or dilution factor are experimentally determined. Preferably, the multiplier ranges from 20 to 40. Although not wanting to be bound by any particular theory regarding the multiplier and/or dilution factor, it is believed that because a water source is used, preferably from a known, specific source, a pre-mix, a selection of base mixtures, and a set procedure for making the strips or liquid, then a multiplier or dilution factor may be utilized to produce a series of related pharmanutrient formulations, which can elicit a range of certain individualized biological effects/responses in an animal or human body (i.e., stimulation, arousal, drowsiness, energy, etc.) within that single series or altered utilizing a different series.

It will also be understood that the base mixture can also optionally be varied in intensity or effectiveness by aging the base mixture for a period of time ranging from about 48 hours to about 240 hours. By aging the base mixture, it has been observed that the effects in the ranges as described in Example 15 below could be achieved and/or maintained. It is believed that the life span or shelf-life of the base mixture alone is approximately twenty-eight days if base mixture aging is utilized in the spirit and scope of the presently described technology.

After any optional dilution and/or aging steps, the mixture containing water, base mixture, and pre-mix is configured into a final, finished formulation for delivery to an animal or human which substantially avoids first-pass metabolism. Suitable and preferred delivery systems are discussed in detail below. Again, while not limited to any one theory, it is believed that by utilizing a delivery system which bypasses first-pass metabolism, the vitamins, minerals, amino acids, co-enzymes, and/or other nutrients as well as pharmacologically active ingredients are more readily made available to the body (e.g., increased "bioavailability"). It is also believed that the avoidance of transport mechanism saturation and excretion of excess ingredients permits the use of much lower amounts/dosages of components than in conventional pharmanutrients or dietary supplements, while still providing beneficial biological or therapeutic effects/responses/affects.

Further, due to decreased dosages, it is believed that side effects of nutrients and pharmacologically active ingredients are minimized or prevented.

Moreover, utilizing lower amounts/dosages of ingredients allows for multiple uses of a single or related formulation, or use of another type of formulation, as an individual's biological need or desired response varies throughout each dosing period (e.g., each 24 hours, 6 hours, 1 hour, or 30 minutes period and the like). Furthermore, it is believed that such individualized responsive dosing is possible in part because the dosage level of any vitamin, mineral, amino acid, co-enzyme, or other nutrient contained in the final formulation (i.e., the final oral strip, liquid drops, capsules, troches, lozenges, etc.) of the present technology are less than about 25% of the RDA or UL of such vitamin, mineral, amino acid, co-enzyme, or other nutrient. More preferably, the dosage levels are less than about 10% or less than 1% of the RDA or UL, and most preferably, less than about 0.10% or about 0.01% of the RDA or UL. Some preferred embodiments have dosage levels of less than about 0.001% of the RDA or UL.

When referred to in the instant technology, the UL is defined as the maximum level of daily intake of any vitamin, mineral, amino acid, co-enzyme, or other nutrient component that is likely to pose no risk of adverse effects, and the RDA is defined as the Recommended Dietary Allowance. Both values are preferably those published by the Food and Nutrition Board of the National Research Council, for Males 19-30 years old. See Example 16: RDA/UL for Some Nutrients. It will be understood, however, by those skilled in the art that the present technology is not limited to those vitamins, minerals, amino acids, co-enzymes, or other nutrient components for which RDA values or UL values have been established by a governing body, and may encompass any nutrient component or composition.

Furthermore, based on known amounts of vitamin, mineral, amino acid, co-enzyme, or other nutrients in a pre-mix or base composition, a known, but optional dilution factor or multiplication factor, and further based on a selected, constant process for producing a final nutrient formulation, the final dosage amounts of any components in the final nutrient formulation of the present technology (i.e., the final oral strip, liquid drops, sprays (such as nasal sprays), capsules, coatings, troches, lozenges, etc.), can be calculated. The same optional dilution and multiplication factor calculation methodology can also be applied to the pharmaceutically active ingredient component of the presently described technology. However, it should again be understood by those skilled in the art that any dilution step is optional with respect to the inclusion of the vitamins, minerals, amino acids, co-enzymes, or other nutrients in a pre-mix or base composition. Thus, it is contemplated that various embodiments of the present technology can be final formulations in which a known dilution factor has not been applied to arrive at those formulations.

With respect to pharmacologically active ingredient component, the present technology contemplates providing such active ingredient components with the nutrient components in a variety of dosage forms (i.e., incorporation of the components together to form one unitary dosage form, or as a separate dosage forms given together at the same time or at separate times) and types of administration modalities.

For example, in one embodiment of the present technology, the nutrient component and the pharmacologically active ingredient can be incorporated together into a final dosage form for administration as a singular dose form to an individual. In another embodiment, the nutrient component of the presently described technology can be administered as a separate dosage form to an individual followed by the administration of the pharmacologically active ingredient component in a further separate dosage form.

In yet another embodiment of the presently described technology, there is contemplated the administration of a portion of the dose of the pharmacologically active ingredient component (i.e., a bolus dose) in a separate dosage form followed by the administration of the dose of the nutrient component in a separate dosage form with subsequent administration of the remainder of the dose of the pharmacologically active ingredient in further separate dosage form. It should be understood that for this particular embodiment, the nutrient component can be given alternatively as a bolus dose in the fashion described above. Thus, the presently described technology envisages a variety of combined and singular component dosage forms, and routes of administration.

After the above described final pharmanutrient formulation is produced, the foregoing process steps may be repeated one or more times, preferably five or more times, and most preferably, ten or more times to produce different doses of a formulation for a particular "series" of that formulation, or different types of formulations for different series to generate one or more individualized biological responses/effects/affects and/or therapeutic responses/effects/affects as desired. Thus, either a different base mixture is selected, or a different dilution or multiplication factor is selected, to produce a system of pharmanutrient compositions capable of being utilized to generate a variety of biological responses, potency of such responses, or frequency of such responses, which are utilized in individualized, responsive dosing regimens (i.e., the various series allow for targeted biological response or therapeutic effect dosing also known herein as "bio-tuning").

For example, a manufacturer may efficiently create a number of different series of the nutrient part of the present technology, such as illustrative Series S, Series T, Series U, Series V, Series K, Series L, Series M, Series N, Series X, and Series W, by utilizing different base mixtures. Examples 4 through 13 set forth below describe preferred base compositions for creation of the foregoing series. Each series may generate a desired and distinct biological effect, affect, or responses, or may overlap slightly in degree of the same response/effect/affect. Within each series, a manufacturer may utilize differing dilution or multiplication factors to efficiently create a gradient of biological responses, etc. One example of an area of impact would be the generation of an energy gradient from sleep (low energy) to awake and on to active high energy. Additionally, Examples 3 and 15 set forth below provide illustrative examples of a gradient of dilution factors and corresponding biological affects/effects/responses observed within a given series. (Series S).

Further, the present technology contemplates alternative manners in which the nutrient(s) and pharmacologically active ingredient(s) of the present technology may be delivered/administered to a human or animal. In one alternative embodiment, the nutrient component and pharmacologically active ingredient are not combined to form a final unitary formulation, but rather are delivered/administered separately. For example, the nutrient aspect of the final desired formulation can be provided to the human or animal as a predisposition composition prior to application/administration of the pharmacologically active ingredient. The same administration pattern can also be utilized where the nutrient aspect of the final formulation is administered to a human or animal followed by a portion of the dose (e.g., a bolus dose) of the pharmacologically active ingredient and subsequent maintenance dose of the same to achieve an improved pharmacokinetic profile.

Below is a detailed description of each of the preferred steps and components in the presently described technology for producing an individualized responsive dosing pharmanutrient system. The compositions of the present technology can include any of the water-soluble and/or fat-soluble vitamins, a coenzyme such as Q10, essential and/or non-essential amino acids, and minerals including without limitation calcium, phosphorus, magnesium, sodium, potassium, chloride, chromium, copper, fluoride, iodine, iron, manganese, molybdenum, selenium, zinc, combinations thereof, and/or derivatives thereof. The presently described technology can also include other ingredients, for example, nitrate, nitrite, folic acid, other nutrients, organic substrates (e.g., yeast, oat, or barley beta-glucans, glucosamine, or chondroitin), inorganic or synthetic substrates (e.g., methylsulfonylmethane), stimulants such as caffeine, combinations thereof, and derivatives thereof. It is also contemplated that the compositions of the present technology may further include pharmacologically active ingredients.

Water

The water can vary from source to source, but preferably contains at least one mineral and optionally, at least one nitrate and at least one nitrite. Most preferably, the presently described technology utilizes water from an Appalachia water source, preferably a water source from the Eastern slope of the Shenandoah Valley. Different water sources would require empirical analysis of its constituents to ensure that the dosage amounts are consistent with spirit of the presently described technology. For example, the base composition multiplier could be changed in order to obtain an adjusted base with a preferred compositional make-up in light of a different water source.

The water is preferably filtered to purify and refine it from the selected water-source. The filter is preferably a commercially available filter having a pore size of about 0.1 microns. However, it should be understood by those skilled in the art that a filter having a pore size of about 0.1 microns to about 0.5 microns can be used within the spirit and scope of the present technology with a pore size of about 0.1 microns to about 0.25 microns being more preferred and a pore size of about 0.1 microns being most preferred. Further, it will be appreciated by those skilled in the art that one may select a suitable filter having a pore size as described above depending upon the quality of water used to make the formulations described herein. An example of components that the filtered water can include, and tolerances for the amounts of those components, is set forth below:

Nitrate 0-0.10 mg/L+25%
Nitrite 0-0.01 mg/L+25%
Calcium 0-12.4 mg/L+25%
Chromium 0-0.001 mg/L+25%
Magnesium 0-5.8 mg/L+25%
Manganese 0-0.001 mg/L+25%
Potassium 0-1.4 mg/L+25%
Sodium 0-1.6 mg/L+25%

Any of these preferred components of the water may range from 0 to +25%. The pH of the water can range from about 5 to about 7.5. Preferably, the pH of the water is about 7.50 at 25 degrees Celsius.

Base Mixture

Preferably, a selection of base mixtures is provided so that various base mixtures may be utilized to create different series of final formulations. It is also preferable that each base mixture is configured to generate a desired biological response/effect/affect and/or therapeutic response/effect/affect. Either completely different or overlapping biological or therapeutic responses may be generated by different base mixtures. Additionally, each of the base mixtures may already contain a pre-mix with constant compositional make-up. The pre-mix need not be identified as such, but may merely contain at least two or more vitamins, mineral, amino acids, or other nutrients which can remain constant (i.e., in relative proportion to one another) within each base mixture.

Moreover, its is preferable to the filter the base mixture to remove particulate matter in the mixture prior to further processing and/or inclusion of the pharmacologically active ingredient. Any conventional particular removal filter may be utilized for this purposes. For example, a filter having a pore size of from about 0.1 microns to about 0.5 microns is suitable for this purpose. However, varying pore size filters achieving particular removal are included within the spirit and scope for use with the presently described technology.

The components of the base mixture preferably comprise at least two of the following: magnesium chloride, sodium chloride, potassium chloride, calcium chloride, ascorbic acid, caffeine, niacin, potassium benzoate, chromium picolinate, chromium, polynicolinate, coenzyme Q10, L-glutamine, potassium sorbate, calcium ascorbate, sodium nitrite, L-arginine, or sodium ascorbate. More preferably, the base mixture comprises at least five of the foregoing (i.e., amino acids, organic substrates, inorganic or synthetic substrates, minerals, vitamins, etc.).

Additionally as noted above, it is also contemplated that the pharmanutrient compositions of the present technology may further include pharmacologically active ingredients. Preferably, the pharmacologically active ingredient is incorporated as a component of the base mixture. However, it should be understood by those skilled in the art that the pharmacologically active ingredient may be incorporated into any of the steps and/or base mixtures, pre-mixes, or water of the presently described technology prior to final formulation processing into a delivery system or vehicle.

Suitable pharmacologically active ingredients which maybe utilized within the spirit and scope of the present technology include, but are not limited to blood modifiers, hormonal agents, diuretic agents, cardiovascular agents, respiratory agents, anti-neoplastic agents, systemic anti-infective agents, central nervous system agents, gastrointestinal agents, local anti-infective agents, and combinations or derivatives thereof.

The dose of the pharmacologically active ingredient present in any final formulation of the present technology may range from about 0.0000001 milligram (mg) or greater. Thus, it should be envisaged by those of skill in the art that the dose of the pharmacologically active ingredient utilized in the spirit and scope of the present technology may be adjusted as necessary for formulation processing relative to the biological response/therapeutic effect/affect desired. Moreover, it should be appreciated by those skilled in the art that the present technology envisages the suitability of prescription as well as non-prescription or over-the-counter ("OTC") medications for use in the formulations described herein. Further, it is also within the spirit and scope of the present technology that the processing steps of the final pharmanutrient formulations may also be adapted to accommodate future pharmaceutical agents that are developed as long as the incorporation of such agents is not in contradiction with the objectives set forth herein.

Examples of blood modifiers include, but are not limited to vitamin k, vitamin B, anticoagulants (e.g., coumadin, heparin), antiplatelet agents (e.g., ticlopidine, enoxaparin sodium), hemostatic agents, plasma agents (e.g., plasma extenders), combinations thereof, and derivatives thereof.

Examples of hormonal agents include, but are not limited to estrogens, progestins, androgens, growth hormones, posterior pituitary hormones, antidiabetic agents (e.g., alpha glucosidase inhibitors, biguanides, thiazolidinediones, sulfonylureas, insulin), thyroid agents, bisphosphonates, calcitonin, glucose elevating agents (e.g., glucagon, glucose, diazoxide), gallium nitrate, combinations thereof, and derivates thereof.

Examples of renal agents include, but are not limited to thiazide diuretic agents, loop diuretics, potassium sparing diuretics, osmotic diuretics, carbonic anhydrase inhibitors, combinations thereof, and derivatives thereof.

Examples of cardiovascular agents include, but are not limited to cardiac glycosides, phosphodiesterase inhibitors, antianginal agents, antiarrythymic agents, peripheral vasodilators, calcium channel blocking agents, vasopressor agents, alpha- or beta-adrenergic blocking agents, antihyperlipidemic agents, salt substitutes, edetate sodium, combinations thereof, and derivatives thereof.

Examples of respiratory agents include, but are not limited to bronchodilators (e.g., sympathomimetic agents and xanthine derivatives), decongestants, mucolytics, coricosteroids, anticholinergics, antitussives (e.g., narcotics and dextromethorphan), expectorants, antihistamines (e.g., ethanolamines, alkylamines, phenothiazines, piperidines, and ethylenediamines), analgesic agents (e.g., aspirin, acetominophen, salsalate, salsalate derivatives, and opioid agents), combinations thereof, and derivatives thereof.

Examples of anti-neoplastic agents include, but are not limited to immunosuppressive agents, cytotoxic agents, alkylating agents (e.g., busulfan, carboplatin, carmustine, mechlorethamine, melphalan, streptozocin, uracil mustard, and cyclophosphamide), antimetabolite agents (e.g., cytarabine, floxuridine, 5-fluorouracil, fludarabine, gemcitabine, hydroxyurea, thioguanine, and methotrexate), hormones (e.g., anastrozole, biculutamide, estramustine, flutamide, goserelin, and diethystilbestrol), antibiotic type agents (e.g., bleomycin, dactinomycin, daunorubicin, doxorubicin, and idarubicin), mitotic inhibitors (e.g., vinca alkaloids, podophyllotoxin derivatives, and taxanes such as docetaxel), radiopharmaceuticals (e.g., strongtium-89 and chromic phosphate), biological response modifiers (e.g., aldesleuekin, interferon alfa-2a, interferon alfa-2b, interferon gamma-1 B, and interferon alfa-n3), altretamine, asparaginase, BCG, cladribine, tretinoin, topoisomerase I inhibitors, porfimer, combinations thereof, and derivatives thereof.

Examples of anti-infective agents include, but are not limited to antibiotics (e.g., penicillins, cephalosporins, monobactams, fluoroquinolones, marcrolides, tetracyclines, polymixins, lincosamides, aminoglycosides, and vancomycin), antifungals (e.g., miconazole, ketoconazole, and amphotericin B), sulfonamides, antimalarial compounds, antitubercular compounds (e.g., isoniazid, rifampin, and ethambutol HCl), amebicides, antiviral agents (e.g., lamivudine, saquinavir, and ganciclovir sodium), leprostatics, antihelmintics (e.g., mebendazole and pyrantel), urinary anti-infectives (e.g., methylene blue, nalidixic acid, and nitrofurantoin), trimethoprim, trimethoprim-sulfamethoxazole combinations, ethyromycin-sulfamethoxazole combinations, furazolidone, pentamindine isethionate, eflorinithine HCl, atovaquone, trimetrexate glucuronate, combinations thereof, and derivatives thereof.

Examples of central nervous system agents include, but are not limited to central nervous system stimulants (e.g., analeptics, amphetamines, and anorexiants), analgesics (e.g., salicylates, narcotic and non-narcotic agonist, antagonists, and agonist-antagonist combinations, nonsteroidal anti-inflammatory agents, agents for migraine, agents for gout, and central analgesics), antiemetic/antivertigo agents, physchotherapeutic agents (e.g., antianxiety agents, antidepressants agents, antipyschotic agents, and psychotherapeutic agents), sedatives and hypnotics (e.g., barbituates, nonbarbituates, and sleep agents), general anesthetics (e.g., gases and volatile liquids), anticonvulsants, muscle relaxants, antiparkinson agents, combinations thereof, and derivatives thereof.

Examples of gastrointestinal agents include, but are not limited to antacids, sucralfate, gastrointestinal anticholinergic/antispasmodic agents, histamine antagonists, prostaglandins, proton pump inhibitors (e.g., lansoprazole), antiflatulants, gastrointestinal stimulant agents (e.g., metoclopramide and cisapride), digestive enzymes, gastric acidifying agents, hydrocholeretics, gallstone solubilizing agents (e.g., monoctanoin), laxatives (e.g., lactulose, hyperosmolar agents, and bulk-producing agents such as psyllium), antidiarrheals (e.g., loperamide, diphenoxylate/atropine combinations, and bismuth subsalicylate), mesalamine, olsalazine sodium, combinations thereof, and derivatives thereof.

It should be understood by those skilled in the art that prescription (brand or generic) and over-the-counter ("OTC") pharmaceutical agents/active ingredients are suitable for use within the presently described technology and should not be limited to a particular form or production source.

Illustrative examples of base mixtures of the present technology are embodied in Tables 4 through 13 and have been designated as series S, T, U, V, K, L, M, N, X and W. Those examples illustrate the preferred make-up and amounts of the individual ingredients/components of exemplar base compositions, including the amount of vitamin premix used and the amount of any additional components admixed with the vitamin premix. For example, Table 4 illustrates that the base composition for the S series comprises 0.02500 grams of vitamin premix admixed with additional components, including, for example, 0.06000 grams of magnesium chloride. Also shown is the adjustment of each component of the base composition by application of a dilution or multiplication factor to arrive at the adjusted base composition. For illustrative purposes, the multiplier is based upon the dissolution of the selected components in a final volume of 1 gallon of profiled water described herein.

Any base composition multiplier may be experimentally determined in regards to a desired biological affect/effect/response, and is, for illustrative purposes, established relative to that water characterized in Example 2. A multiplication factor is preferably empirically determined so as to compensate for variables. The variables that are taken into consideration can include without limitation: any additional ingredients/components coming from selected water sources used for dissolution; any processing required to arrive a final dosage form; and/or any adjustments required to achieve a desired biological response/effect. The multiplier is empirically derived and can range from a factor of about 20 to about 40. This multiplier is utilized to create a final adjusted base composition, which will achieve the adequate amount of each component per base composition, which can then be further formulated into a specific dosage form and chosen for application based on desired biological affects/effects/responses on any living system, human or otherwise.

For further illustrative purposes, each exemplar series S, T, U, V, K, L, M, N, X and W may be further divided into sub-series based on varying dosage amounts. For example, the S-series may contain subs-series S-1 through S-10 compositional nutraceutic products, which vary in their solids content with S-1 having less solids than S-10 based upon the dilution rate of the S series adjusted base composition. See Example 15. The grouping of compositional products, produced by dilution in the selected water of each of the representative adjusted base composition mixtures, is illustrated in Tables 14-22 for each additional exemplar series T, U, V, K, L, M, N, X and W.

Pre-Mix

The general pre-mix formulation is preferably comprised of pharmaceutical grade vitamins, minerals, amino acids, coenzymes, or other nutrients. Each ingredient is preferably on the United States Food and Drug Administration's Generally Recognized As Safe (GRAS) list. An illustrative example of a standard premix composition of the presently described technology is shown in Example 1 and includes vitamins A, B1, B2, B3, B6, B12, C, D3, E and H, in admixture with folic acid, copper, iron, potassium iodide, calcium carbonate, and zinc. A further embodiment of the present technology includes base compositions containing the vitamin premix composition in addition to any further components/ingredients added to the vitamin premix composition. By way of example, additional components/ingredients added to the vitamin premix to form a base composition may include without limitation magnesium chloride, sodium chloride, potassium chloride, calcium chloride, ascorbic acid, caffeine, niacin, potassium benzoate, chromium picolinate, chromium polynicolinate, coenzyme Q10, L-glutamine, and potassium sorbate, sodium ascorbate, potassium carbonate, calcium ascorbate, calcium carbonate, L-arginine, sodium nitrite, combinations thereof, and derivatives thereof.

In the preferred embodiments of the presently described technology, the compositional make-up of the pre-mix formulation does not vary during processing, or in separate types or series of finished pharmanutrient product. The pre-mix dosage amounts, however, are preferably adjusted through dilution or multiplication of the base mixture.

Delivery System

For the present technology, any dosage form can be utilized. Those dosage forms can include, for example, an oral film, a tablet, a pill, a liquid, a capsule, a lozenge, a troche, a suppository, a transdermal patch, a coating, a nasal spray, a dragee, a slurry, an oral suspension, an oral powder, a power for inhalation, or an emulsion. For this particular technology, dosage administration routes are preferably those that bypass first pass metabolism such as buccal, sublingual, nasal, transdermal, intradermal, intramuscular, intravenous and certain rectal administration routes. This is due to the present technology believing to have enhanced efficacy by circumventing dosage administration routes which would undergo first pass metabolism (oral, in particular).

Compositions of the present technology can be preferably formulated for either parenteral or enteric absorption. Parenteral absorption generally comprises absorption by way other than the gastrointestinal track and without significant first pass metabolism. By way of example and without limitation, parenteral absorption can be pre-gastric (e.g., sublingual or buccal), topical, optical, intravenous, and/or by oral or nasal inhalation. Pre-gastric absorption as used herein comprises absorption of an ingredient from that part of the alimentary canal prior to the stomach, and includes without limitation buccal, sublingual, oropharyngeal and esophageal absorption. It is envisaged that such pre-gastric absorption will occur primarily across the mucous membranes in the mouth, pharynx and oesophagus. The presently described technology, however, is not limited to any one method of delivery, and envisions delivery via any tissue with an adequate rate of absorption, which avoids first pass metabolism.

It is preferred that the composition of the present technology is formulated to promote absorption of ingredient(s)/component(s) of the final pharmanutrient formulation through the buccal, sublingual, pharyngeal and/or esophageal mucous membranes, or into a biological fluid pathway(s) such as the lymphatic system. Without being bound by a particular theory, it is believed that pre-gastric absorption will occur primarily across the mucous or lymphatic membranes in the mouth or oral cavity, pharynx and esophagus. The oral mucosa has a thin epithelium and a rich vascularity that favors absorption. Blood capillaries and lymphatic vessels are extremely close to the surface in these areas and readily absorb the ingredients into the blood stream. The flow is from this area of the mouth to the Carotid Artery, or other suitable route (e.g., other suitable vasculature, nerve, or lymphatic routes and it is envisaged that distribution to the brain and the rest of the body will be rapid, thereby resulting in greatly enhanced efficacy and/or rates of response/effect/affect. Thus, it is believed that the formulations of the presently described technology have the capability of affecting/effecting a variety of biological responses such as sympathetic, parasympathetic, immunological, metabolistic, endocrinological, responses and the like.

Again, although not wanting to be bound by any particular theory, it is further believed that the pharmanutrient formulation(s) of the present technology through enhanced bioavailability have the capability of interacting with the regulatory systems of a human or animal body.

For example, it is believed that the enhanced delivery system(s) acquiring enhanced bioavailability of the present technology interact primarily with, but not limited to the central nervous system, for example, the hypothalmous-pituitary-thyroid axis ("H-P-T" axis), to generate a targeted biochemical signal (i.e., release of neurochemical transmitters and the like from the axis), which in turn is capable of generating a targeted biological/biochemical/therapeutic response/effect/affect depending upon the nutrient and pharmacologically active ingredients provided contained within the pharmanutrient formulation, dosage form utilized, and/or administration modality used.

In other words, it is believed that the pharmanutrient formulations of the present technology have the capability of interacting with the regulatory systems (including, but not limited to sympathetic, parasympathetic, immunological, thyroid, parathyroid, and endocrinological/hormonal) of a human or animal body (i.e., master-switch(es)) to effectuate targeted, zero-order kinetic biological and/or therapeutic responses/effects/affects. Examples of such "master-switches" include, but are not limited to the central nervous system and its sub-component systems such as the H-P-T axis, the hormonal system, the humoral system, the adrenal/renal system (e.g., the renin-angiotensin system), and the like.

It is also envisaged that the compositions of the presently described technology can be formulated to be fast-dispersing and bioadherent for application to the surface of another product intended for absorption (e.g., enteric absorption achieved via an enteric coated formulation) or for release from the surface of another product (e.g., a coated stent structure in which the coating contains the presently described technology). Accordingly, any of the compositions of the presently described technology upon rapid dissolution from the surface of another product can be preferably retained in the oral cavity (or other suitable cavity or surface of a human or animal body) so as to facilitate pre-gastric absorption, while the balance of said other product moves further into the GI tract to undergo enteric absorption.

It is also believed that ingredients absorbed by pre-gastric absorption will pass straight into the systemic circulatory system and thereby avoid the gastrointestinal track and first pass metabolism in the liver. Accordingly, bioavailability of an active ingredient delivered in this way may also be increased. Additionally, the bioavailability of a number of vitamins, minerals, amino acids, co-enzymes, pharmacologically active ingredients, organic substrates, inorganic or synthetic substrates, biological components, and/or other nutrients in concert can also be increased. It is desired that the dose of an ingredient may be minimized, while still producing the desired beneficial effects, with close to zero order kinetics (immediate efficacy) thereby decreasing the required dose and minimalization of undesired side effects. These concentrations may vary and will be selected primarily on the desired biological response and dosage form selected.

U.S. Pat. Nos. 6,596,298; 6,569,463; 5,948,430; 6,592,887; 5,629,003; 6,419,903; and 6,316,029 disclose various delivery systems which may be utilized in the present technology.

One particularly preferred method of delivery, although not limited to any one method, is a consumable oral strip. The dosage form can include by way of example and without limitation, a starch, pectin, and/or cellulose based strip or film that adheres to and dissolves in a mouth of a consumer. A strip formulation is made utilizing conventional film formulation processing and technology. The preferred film formulation is a starch-based film formulation or matrix. Other film formulation matrixes can be utilized such as pectin and other film bases (cellophane tape).

However, it should be understood by those skilled in the art that the present technology may be formulated in such a manner for utilization via a variety of delivery systems. For example, it is envisaged that the present technology may be applied to the surface of a various biological implants (e.g., pace makers, wiring, pumps, cardiac patches, cardiac stents, wound seeding devices, and the like) for release into a localized area. Although not wanting to be bound by any particular theory, it is believed that such a delivery of the present technology can accelerate local cellular repair at the site of delivery, which in turn can accelerate localized healing time of the cellular material and associated tissue.

Based on selected amounts of vitamin, mineral, amino acid, co-enzyme, organic substrate, inorganic or synthetic substrate, biological component, pharmacologically active ingredient, and/or other nutrients in a selected pre-mix or base composition, a selected dilution factor or multiplication factor, and further based on a selected, constant process for producing a final formulation, a final dosage amount of components/ingredients in a finished oral strip may be determined. The dosage level will be determined therefore, by the number of strips made per gallon of the mixture comprising water, final base mixture, and/or pharmacologically active ingredient. Preferably, this rate of strips per gallon of mixture is a constant during processing, such that variation in the finished pharmanutrient product is achieved through the afore-mentioned multiplication and dilution factors. Optionally, the rate of strips per gallon may also be adjusted to vary finished pharmanutrient formulation properties. A conventional oral strip processing method is disclosed in U.S. Pat. No. 6,596,298 to Leung ("the Leung patent").

In preferred methods of strip formulation, approximately 2020 grams of the mixture comprising water, base mixture, and pre-mix (regardless of the dilution factor and/or multiplication factor), excluding the pharmacologically active ingredient is used per 454 grams of strip matrix. Additionally, preferred oral strips have dimensions of approximately 35.356 mm$^3$ with a tolerance of +/−5%. As one illustrative example, in preferred strip formulation processing, when utilizing a K-16 formulation, approximately 19,500 strips may be made from approximately one gallon of K-16.

Individualized Responsive Dosing

Additional embodiments of the present technology include individualized responsive dosing methods, wherein an individual may select from different series or types of nutrients and pharmacologically active ingredients components within a series based on varying need or desired biological response/effect/affect needed throughout each 24 hour period (or in some embodiments, each 6 hour or 1 hour period). The preferred method of dosing provides a selection of one or more (preferably three or more) pharmanutrient formulations comprised of a nutrient component and a pharmacologically active ingredient component in delivery systems which substantially avoid first pass metabolism. Each member of the selected pharmanutrient formulations comprises: (a) at least five or more vitamins, minerals, amino acids, co-enzyme, or other nutrients in amounts no greater than about 25% of the Recommended Daily Allowance (RDA) or Upper Limit (UL); (b) water containing at least one mineral, nitrate, and nitrite, each in an amount less than about 25% of the RDA or UL for that component; and (c) 0.0000001 mg or greater of a pharmacologically active ingredient. Furthermore, the pharmanutrient formulation is separately configured to generate a specific, pre-determined biological response/effect and/or affect.

The different pharmanutrient formulations of the present technology may be configured to generate the following pre-determined biological responses: preventative or remedial anti-aging, hormonal release, cardiovascular outcomes (e.g., decreased hypertension and decreased atherosclerotic plaque deposition), neurochemical release or uptake, glucose modulation, cellular repair, calmness, elimination or excretion of cellular or tissue by-products (e.g., ammonia), enhanced immune modulation and response, cellular metabolism including nucleic acid and amino acid metabolism; energy metabolism, including energy conversion and utilization; mental acuity, including memory and cognitive function; nerve signaling including neuromuscular transmission and propagation; hormone signaling including stimulation of the hypothalamic-pituitary-thyroid axis; management of peripheral and central fatigue, including the enhancement of antioxidant defense systems; the modulation of tissue catabolic activity, the mitigation of episodic and/or chronic stress; and detoxification by the liver including increased alcohol metabolism.

Preferably, each formulated series has a similar, overlapping, or different biological effect(s)/response(s) and/or affect(s), which can be graded within the series. In other words, a series such as exemplary Series S may be anecdotally shown to produce varying levels of energy or relaxation per composition/formulation within the series. Thus, for illustration purposes, the gradient of Example 15 may be observed. Thus, it should be understood by those skilled in the art that more than one desired response/effect/affect can be generated per series and per gradient within a series.

Although not wanting to be bound be any particular theory, it is believed that a series such as the exemplary S series may, for example, enhance biochemical signal processing within cellular tissues to cause a gradient of energy levels observed which are dependent upon the concentration (i.e., solids content) of the composition within the series utilized (i.e., S-1 biological effects v. S-10 biological effects). It is further believed that such energy enhancement effects are due to enhanced cellular radical scavenging, oxygenation, or utilization of GABA as well as tissue responses such as vasodilation or enhanced glomerular filtration. Further believed biological responses/effects/affects of the compositions of the presently described technology are provided above.

Additionally, as previously described, the administration of these formulations to the body in a delivery system which preferably avoids first pass metabolism increases bioavailability of the formulations to the body, which in turn enhances a nutrient or pharmacologically active ingredient component capacity or concentrations at a cellular level to the tissues, which in turn again with increased capacity improves cellular absorptive capacity of the component/ingredient leading to a biochemical signal being generated to those tissues and a biological/biochemical/therapeutic response produced. Thus, it was surprisingly and unexpectedly discovered that the pharmanutrient formulations of the present technology exhibited such individualized, responsive dosing regimen capabilities (i.e., individualized "bio-tuning").

As a result, an individual or health care provider may select one of the series to begin with and attempt to achieve a particular desired biological or therapeutic response.

For example, an individual/health care provider may select the S-series to achieve enhanced levels of energy or drowsiness depending upon which composition within the S-series is selected. If the individual/health care provider selects an illustrative S-1 composition, then the individual/patient could preferably take 1 strip or 1 drop of the composition at a time to try and achieve the "energy" effect/affect desired. If the response/effect/affect is not achieved, then the individual/patient may continue with a strip by strip or drop by drop approach to try and achieve the particular biological effect(/affect)/biological response/therapeutic effect(/affect) desired with that particular composition of the series. This particular dosage methodology is an individualized responsive dosing or titration approach. For a liquid formulation, an individual/health care provider may preferably begin with 5 drops and continue to titrate drop by drop to attempt to achieve the desired biological response/effect/affect. For comparison purposes, 120 drops equal 1 Teaspoon. Such an approach also improves the individual's compliance in appropriately taking and maintaining their dosing regimen because the desired biological effect/response (which may be reached through titration, if necessary) can be achieved. Thus, it is believed the pharmanutrient compositions and systems of the presently described technology reduce or prevent mal- or non-compliant administration of the dosage forms described herein which in turn improves the temporal dynamics of the individual while taking such formulations.

If the composition of the series still does not provide the biological response/biological effect (or affect)/therapeutic effect (or affect) the individual or health care provider desires, then the individual or health care provider can select a high solids content formulation within the series such as, for example, S-2 to S-10 to try and achieve the desired effect (or change of effect, i.e., from sleep to energy) on a strip by strip or drop by drop basis again.

Finally, if the individual/health care provider still does not achieve the desired biological response/biological effect (or affect)/therapeutic effect (or affect) with that particular series/formulation, then the individual or health care provider may select another series and continue with the foregoing approaches again to see if the desired response/effect can be achieved. However, a different series/formulation may generate completely different biological responses/biological effects (or affects)/therapeutic effects (or affects) (i.e., outcomes such as calmness for one formulation versus decreased hypertension for another formulation), or may overlap in its response/effect/affect (i.e., decreased energy and decreased anxiety exhibited by one formulation). In addition, it should be understood by those skilled in the art that the present technology envisages the additive and synergistic effects that can occur with and between the various formulations set forth herein. Moreover, it is also contemplated that the present technology can also exhibit various agonist and antagonist effects as well.

For example, S-1 is more suitably directed to sleep promotion. Likewise, a T-1 formulation will have a different affect/effect/response than an S-1 formulation, although certain T Series formulations may have similar affects/effects/responses to certain S Series formulations (i.e., affect/effect/response overlap (or additively or synergistically if given together)). Yet, the same individualized responsive dosing approach is utilized regardless of the series selected. It should also be understood by those skilled in the art that by differing the ingredients of the various formulations of the present technology that one is able to achieve differing biological affects/effects, outcomes, and/or responses as well. For example, the inclusion of ascorbates in some formulations of the present technology rather than a chloride based salt allows for the reduction in heart burn potential in those individuals that take the ascorbate-based formulation.

As previously described, the overall dosing methodology above is referred to as individualized responsive dosing since the individual is dosing his or herself (or through medical supervision with respect to prescription only pharmacologically active ingredients) in a stepwise fashion to attempt to achieve the desired biological/biochemical signal and resultant biological/therapeutic effect, affect response, or outcome. Conventional pharmanutrient regimens (i.e., standard and/or mega-dosing) do not allow patients and/or health care providers to variably and individually dose an individual/patient based upon that individual's biological responses, biochemical signals, or therapeutic responses in an efficient and effective manner (i.e., zero-order kinetics without first-pass metabolistic effects) because conventional pharmanutrient compositions are a one standard or mega-dose/one dosing-regimen fits all type approach which would be counter to the presently described technology's individualized responsive dosing approach.

The following examples describe some of the preferred embodiments of the present technology without limiting the technology thereto. Other embodiments include, but are not limited to, those described in the above written description, including additional or alternative components, alternative concentrations, and additional or alternative properties and uses.

EXAMPLES

Example 1

Pre-Mix Composition

| Component | Amount | Component | Amount |
|---|---|---|---|
| Vitamin A | 6000 U.S.P. | Vitamin $D_3$ | 480 U.S.P. |
| Vitamin $B_1$ | 0.00519 mg | Vitamin E | 35 U.S.P. |
| Vitamin $B_2$ | 0.00392 mg | Vitamin H | 0.00045 ug |

-continued

| Component | Amount | Component | Amount |
| --- | --- | --- | --- |
| Vitamin $B_3$ | 0.05 mg | Folic Acid | 0.00048 ug |
| Vitamin $B_6$ | 0.05 | Copper | 0.0022 mg |
| Vitamin $B_{12}$ | 0.000015 ug | Iron | 0.0191 mg |
| Vitamin C | 0.15 mg | Potassium Iodide | 0.000165 ug |
| Zinc | 16.1 mg | Calcium carbonate | 0.1 mg |

Example 2

Water Composition

| Analyte | Result | Units |
| --- | --- | --- |
| Nitrate | <0.10 | mg/L |
| Nitrite | <0.01 | mg/L |
| Calcium | 12.4 | mg/L |
| Chromium | <0.001 | mg/L |
| Magnesium | 5.8 | mg/L |
| Manganese | <0.001 | mg/L |
| Potassium | 1.4 | mg/L |
| Sodium | 1.6 | mg/L |

Example 3

Typical Method for Optional Dilution

| Sub-series | Dilution rate to 1 gallon mixture for processing into final product |
| --- | --- |
| S-1 | 0.5 oz to 1 gallon |
| S-2 | 1 oz to 1 gallon |
| S-3 | 2 oz to 1 gallon |
| S-4 | 3 oz to 1 gallon |
| S-5 | 4 oz to 1 gallon |
| S-6 | 5 oz to 1 gallon |
| S-7 | 6 oz to 1 gallon |
| S-8 | 7 oz to 1 gallon |
| S-9 | 8 oz to 1 gallon |
| S-10 | 9 oz to 1 gallon |
| S-11 | 10 oz to 1 gallon |
| S-16 | 15 oz to 1 gallon |
| S-21 | 20 oz to 1 gallon |
| S-26 | 25 oz to 1 gallon |

Dilution Method for all S Series products - Mix initial proscribed amount of Base Mixture with the same quantity of profiled water. Agitate for 1 minute per dilution. Repeat until 1 gallon of finished mixture is produced. For example, 8 such steps are required for S-1. Preferably, wait about 8 hours between dilution steps.

Example 4

Exemplar Base Composition for Series S

| Base Composition | Base Amount (grams) | Multiplier | Adjusted Base Composition (Dissolved in 1 gallon Select Water = Adjusted Base Composition Mixture) |
| --- | --- | --- | --- |
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |
| Pharmaceutical active ingredient | 0.01 μ/mg/g | $\geq 1$ | $\geq 1$ μg/mg/g |

Example 5

Exemplar Base Composition for Series T

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |
| Pharmaceutical Active ingredient | 0.01 µ/mg/g | ≧1 | ≧1 µg/mg/g |

Example 6

Exemplar Base Composition for Series U

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |
| Pharmaceutical active ingredient | 0.01 µ/mg/g | ≧1 | ≧1 µ/mg/g |

Example 7

Exemplar Base Composition for Series V

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |
| Pharmaceutical active ingredient | 0.01 µ/mg/g | ≧1 | ≧1 µ/mg/g |

Example 8

Exemplar Base Composition for Series K

| Base Composition | Base Composition (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |
| Pharmaceutical active ingredient | 0.01 µ/mg/g | ≧1 | ≧1 µ/mg/g |

Example 9

Exemplar Base Composition for Series L

| Base Composition | Base Amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.09500 g | 23 | 2.185 g |

| Base Composition | Base Amount (grams) | Multiplier | Adjusted Base Composition (Dissolved in 1 gallon Select Water = Adjusted Base Composition Mixture) |
|---|---|---|---|
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |
| Pharmaceutical active ingredient | 0.01 μ/mg/g | ≧1 | ≧1 μ/mg/g |

Example 10

Exemplar Base Composition for Series M

| Base Composition | Base Amount (Grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid(ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |
| Pharmaceutical active ingredient | 0.01 μ/mg/g | ≧1 | ≧1 μ/mg/g |

Example 11

Exemplar Base Composition for Series N

| Base Composition | Base Amount (Grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |

-continued

| Base Composition | Base Amount (Grams) | Multiplier | Adjusted Base Composition (Dissolved in 1 gallon Select Water = Adjusted Base Composition Mixture) |
|---|---|---|---|
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |
| Pharmacologically active ingredient | 0.01 μ/mg/g | ≧1 | ≧1 μ/mg/g |

Example 12

Exemplar Base Composition for Series W

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| L-Arginine | 0.25000 g | 23 | 5.75 g |
| Potassium sorbate | 0.10000 g | 23 | 2.3 g |
| Sodium nitrite | 0.07250 g | 23 | 1.6675 g |
| Pharmacologically active ingredient | 0.01 μ/m g/g | ≧1 | ≧1 μ/mg/g |

Example 13

Exemplar Base Composition for Series X

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |

-continued

| Base Composition | Base amount (grams) | Multiplier | Adjusted Base Composition (Dissolved in 1 gallon Select Water = Adjusted Base Composition Mixture) |
|---|---|---|---|
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| L-Arginine | 0.25000 g | 23 | 5.75 g |
| Potassium sorbate | 0.10000 g | 23 | 2.3 g |
| Pharmacologically active ingredient | 0.01 μ/mg/g | ≧1 | ≧1 μ/mg/g |

Example 14

Typical Oral Strip Ingredients (W/O Inclusion of Pharmacologically Active Ingredient)

| Component | Results (mg/strip) |
|---|---|
| Nitrate | <0.002 |
| Nitrite | <0.0002 |
| Calcium | 0.1279 |
| Chromium | 0.000055 |
| Magnesium | 0.037 |
| Manganese | 0.00001 |
| Potassium | 0.23 |
| Sodium | 2.442 |

Example 15

One Examplar of a Response/Effect/Affect Gradient Within a Series

S-1 Generates a biochemical signal for sleep

S-2 Generates a biochemical signal for relaxation

S-3 Generates a biochemical signal for calmness

S-4 Generates a biochemical signal for decreased anxiety

S-5 Generates a biochemical signal for increased mental alertness

S6-S7 Generates a biochemical signal for increased mental acuity and focus

S-8 Generates a mild biochemical signal for increased energy

S-9 Generates a medium biochemical signal for further increased energy

S-10 Generates a strong biochemical signal for enhanced energy sensation.

Example 16

RDA/UL Values for Some Nutrients

| Nutrient | RDA (mg/day) | UL (mg/day) |
|---|---|---|
| Folate | 0.4 | 1 |
| Niacin | 16 | 35 |
| Pantothenic Acid | 5 | ND |
| Vitamin B2 | 1.3 | ND |
| Vitamin B1 | 1.2 | ND |
| Vitamin A | 0.9 | 3 |
| Vitamin B6 | 1.3 | 100 |
| Vitamin B12 | 2.4 | ND |
| Vitamin C | 75 | 2000 |
| Vitamin D | 5 | 50 |
| Vitamin E | 15 | 1000 |
| Vitamin K | 0.12 | ND |
| Calcium | 1000 | 2500 |
| Chromium | 0.035 | ND |
| Copper | 0.9 | 10 |
| Fluoride | 4 | 10 |
| Iodine | 0.15 | 1.1 |
| Iron | 8 | 45 |
| Magnesium | 320 | 350 |
| Manganese | 2.3 | 11 |
| Molybdenum | 0.045 | 2 |
| Phosphorus | 700 | 4000 |
| Selenium | 0.055 | 0.4 |
| Vanadium | ND | 1.8 |
| Zinc | 11 | 40 |

Example 17

Typical RDA/UL Percentages of an Exemplar Final Formulation/Profile (5 Drops)

| Ingredients | Base amounts (g) | Diluted Amounts Per Gallon (g) | Amount in 5 drops (g) | US Dietary Guidelines (For Men 25-50 years old) (g) | Percentage Difference between Dosage and the US Dietary Guidelines |
|---|---|---|---|---|---|
| Magnesium (Chloride) | 1.3800 | 5.39E−03 | 2.77E−07 | 0.35 RDA | 0.00007920% |
| Sodium (Chloride) | 2.0700 | 8.09E−03 | 4.16E−07 | 2.4 RDA | 0.00001733% |
| Potassium (Chloride) | 2.0700 | 8.09E−03 | 4.16E−07 | 4 DV | 0.00001040% |

-continued

| Ingredients | Base amounts (g) | Diluted Amounts Per Gallon (g) | Amount in 5 drops (g) | US Dietary Guidelines (For Men 25-50 years old) (g) | | Percentage Difference between Dosage and the US Dietary Guidelines |
|---|---|---|---|---|---|---|
| Calcium (Chloride) | 1.3800 | 5.39E−03 | 2.77E−07 | 1.2 | RDA | 0.00002310% |
| Ascorbic Acid | 11.5000 | 4.49E−02 | 2.31E−06 | 2 | UL | 0.00011551% |
| Caffeine | 1.0925 | 4.27E−03 | 2.19E−07 | 0.24 | | 0.00009144% |
| Niacin | 0.2300 | 8.98E−04 | 4.62E−08 | 0.035 | UL | 0.00013201% |
| Potassium (Benzoate) | 1.0350 | 4.04E−03 | 2.08E−07 | 4 | DV | 0.00000520% |
| Chromium (Picolinate) | 0.0043 | 1.68E−05 | 8.64E−10 | 0.00012 | DV | 0.00071999% |
| Chromium (Polynicolinate) | 0.0043 | 1.68E−05 | 8.64E−10 | 0.00012 | DV | 0.00071999% |
| Coenzyme Q10 | 0.7188 | 2.81E−03 | 1.44E−07 | N/A | | |
| L-Glutamine | 5.7500 | 2.25E−02 | 1.16E−06 | N/A | | |
| Potassium (Sorbate) | 2.3000 | 8.98E−03 | 4.62E−07 | 4 | DV | 0.00001155% |
| Vitamin A | 0.2371 | 9.26E−04 | 4.76E−08 | 2 | | 0.00000238% |
| Vitamin B1 | 0.0041 | 1.62E−05 | 8.33E−10 | 0.0011 | RDA | 0.00007569% |
| Vitamin B2 | 0.0031 | 1.22E−05 | 6.29E−10 | 0.0013 | RDA | 0.00004837% |
| Vitamin B3 | 0.0399 | 1.56E−04 | 8.02E−09 | 0.035 | UL | 0.00002292% |
| Vitamin B6 | 0.0399 | 1.56E−04 | 8.02E−09 | 0.1 | UL | 0.00000802% |
| Vitamin B12 | 0.0000 | 4.68E−08 | 2.41E−12 | 0.0000024 | RDA | 0.00010027% |
| Vitamin C | 0.1198 | 4.68E−04 | 2.41E−08 | 2 | UL | 0.00000120% |
| Vitamin D3 | 0.0190 | 7.41E−05 | 3.81E−09 | 0.00005 | UL | 0.00762078% |
| Vitamin E | 0.0014 | 5.40E−06 | 2.78E−10 | 1 | UL | 0.00000003% |
| Vitamin H | 0.0004 | 1.40E−06 | 7.22E−11 | 0.00003 | AI | 0.00024064% |
| Folic Acid | 0.0004 | 1.50E−06 | 7.70E−11 | 0.001 | RDA | 0.00000770% |
| Copper | 0.0018 | 6.86E−06 | 3.53E−10 | 0.002 | DV | 0.00017765% |
| Iron | 0.0153 | 5.96E−05 | 3.06E−09 | 0.01 | RDA | 0.00003064% |
| Potassium (Iodide) | 0.0001 | 5.12E−07 | 2.64E−11 | 4 | DV | 0.00000000% |
| Calcium (Carbonate) | 0.0799 | 3.12E−04 | 1.60E−08 | 1.2 | RDA | 0.00000134% |
| Zinc | 0.0129 | 5.02E−05 | 2.58E−09 | 0.015 | RDA | 0.00001722% |

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

What is claimed:

1. A pharmanutrient dosing method comprising selecting from two or more different formulations provided as oral strips, sublingual liquids or sprays which substantially avoid first pass metabolism, wherein each pharmanutrient formulation comprises five or more of the following in an amount equal to about 5 drops in a liquid:

about $2.77 \times 10^{-7}$ g magnesium;
about $4.16 \times 10^{-7}$ g sodium;
about $1.09 \times 10^{-6}$ g potassium;
about $2.93 \times 10^{-7}$ g calcium;
about $2.31 \times 10^{-6}$ g ascorbic acid;
about $2.19 \times 10^{-7}$ g caffeine;
about $4.62 \times 10^{-8}$ g niacin;
about $1.73 \times 10^{-9}$ g chromium;
about $1.44 \times 10^{-7}$ g coenzyme Q-10;
about $1.16 \times 10^{-6}$ g L-glutamine
about $4.76 \times 10^{-8}$ g vitamin A;
about $8.33 \times 10^{-10}$ g vitamin B1;
about $6.29 \times 10^{-10}$ g vitamin B2;
about $8.02 \times 10^{-9}$ g vitamin B3;
about $8.02 \times 10^{-9}$ g vitamin B6;
about $2.41 \times 10^{-12}$ g vitamin B12;
about $2.41 \times 10^{-8}$ g vitamin C;
about $3.81 \times 10^{-9}$ g vitamin D3;
about $2.78 \times 10^{-10}$ g vitamin E;
about $7.22 \times 10^{-11}$ g vitamin H;
about $7.7 \times 10^{-11}$ g folic acid;
about $3.53 \times 10^{-10}$ g copper;
about $3.06 \times 10^{-9}$ g iron; or
about $2.58 \times 10^{-9}$ g zinc,
and further wherein at least one of the two or more different formulations comprises:
at least one other pharmacologically active ingredient selected from the group consisting of analgesic agents, antihistamines, antacids, antiflatulants, laxatives, antidiarrheals, and stimulants; and
administering the selected formulation to a recipient which substantially avoids first pass metabolism.

2. The method of claim 1, wherein the vitamins, minerals, amino acids, or co-enzyme Q-10 include at least five or more of the members of the group consisting of: vitamin A, vitamin B1, vitamin B2, vitamin B3, vitamin B6, vitamin B12, vitamin C, vitamin D3, vitamin E, vitamin H, folic acid, copper, iron, potassium iodide, calcium carbonate, and zinc.

* * * * *